(12) United States Patent
Emery et al.

(10) Patent No.: US 7,452,539 B2
(45) Date of Patent: Nov. 18, 2008

(54) STABILIZING POLYPEPTIDES WHICH HAVE BEEN EXPOSED TO UREA

(75) Inventors: Jefferson C. Emery, Foster City, CA (US); Paul J. McDonald, San Francisco, CA (US); Rhona M. O'Leary, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 574 days.

(21) Appl. No.: 10/316,694

(22) Filed: Dec. 11, 2002

(65) Prior Publication Data

US 2003/0118583 A1 Jun. 26, 2003

Related U.S. Application Data

(60) Provisional application No. 60/341,891, filed on Dec. 19, 2001.

(51) Int. Cl.
*A61K 39/395* (2006.01)
*C07K 16/00* (2006.01)

(52) U.S. Cl. ............... 424/176.1; 422/28; 424/177.1; 514/2; 530/350; 530/380; 530/381; 530/390.1; 530/390.5; 530/413

(58) Field of Classification Search ............... 422/28; 424/176.1, 177.1; 530/350, 380–384, 390.1, 530/390.5, 413; 514/2; 436/535
See application file for complete search history.

(56) References Cited

U.S. PATENT DOCUMENTS

| | | | |
|---|---|---|---|
| 4,605,513 A | 8/1986 | DiMarchi | 530/303 |
| 5,429,746 A | 7/1995 | Shadle et al. | 210/635 |
| 5,439,829 A * | 8/1995 | Anderson et al. | 436/518 |
| 5,534,621 A * | 7/1996 | Ladner et al. | 530/413 |
| 5,633,349 A * | 5/1997 | Reichl | 530/364 |
| 5,770,199 A | 6/1998 | Eibl et al. | 424/176.1 |
| 5,811,098 A | 9/1998 | Plowman et al. | 424/178.1 |
| 6,004,555 A | 12/1999 | Thorpe et al. | 424/181.1 |
| 6,127,526 A | 10/2000 | Blank | 530/413 |
| 6,333,348 B1 * | 12/2001 | Vogel et al. | 514/449 |
| 2002/0031515 A1 * | 3/2002 | Caligiuri et al. | 424/155.1 |
| 2003/0118583 A1 * | 6/2003 | Emery et al. | 424/130.1 |

FOREIGN PATENT DOCUMENTS

WO WO 99/57134 11/1999

OTHER PUBLICATIONS

Randall et al, Jour. Biochem. Molec. Biol. Biophys., 2, 51, 1998.*
Hudson et al, Practical Immunology, 2$^{nd}$ ed., Blackwell Scientific Publications, 1980, p. 346.*
Sober (Ed.), Handbook of Biochemistry, The Chemical Rubber Co., 1968, p. B-55.*
White et al, Principles of Biochemistry, Third Edition, McGraw-Hill Book Company, 1964. p. 627.*
Goller and Galinski., "Protection of a Model Enzyme (Lactate Dehydrogenase) Against Heat, Urea and Freeze-Thaw Treatment by Compatible Solute Additives." *J. Molecular Catalysis B: Enzymatic* 7:37-45 (1999).
Ou, Wen-Bin et al., "Molecular Mechanism for Osmolyte Protection of Creatine Kinase Against Guanidine Denaturation." *European Journal of Biochemistry* 268:5901-5911 (2001).
Albanell et al., "Trastuzumab, a humanized anti-HER2 monoclonal antibody, for the treatment of breast cancer" *Drugs of Today* 35(12) : 931-946 (1999).
Lin, Maio-Fang, et al., "Ion chromatographic quantification of cyanate in urea solutions: estimation of the efficiency of cyanate scavengers for use in recombinant protein manufacturing", *Journal of Chromatography B*, vol. 803, pp. 353-362 (2004).

* cited by examiner

*Primary Examiner*—David A Saunders
(74) *Attorney, Agent, or Firm*—Wendy M. Lee; Ginger R. Dreger; Goodwin Procter LLP

(57) ABSTRACT

Methods for stabilizing polypeptides, such as anti-HER2 antibodies, which have been exposed to urea.

22 Claims, 10 Drawing Sheets

LIGHT CHAIN

```
1                          15                          30                          45
DIQMTQSPSSLSASVGDRVTITCRASQDVNTAVAWYQQKPGKAPK
46                         60                          75                          90
LLIYSASFLYSGVPSRFSGSRSGTDFTLTISSLQPEDFATYYCQQ
91                         105                         120                         135
HYTTPPTFGQGTKVEIKRTVAAPSVFIFPPSDEQLKSGTASVVCL
136                        150                         165                         180
LNNFYPREAKVQWKVDNALQSGNSQESVTEQDSKDSTYSLSSTLT
181                        195                         210   214
LSKADYEKHKVYACEVTHQGLSSPVTKSFNRGEC    SEQ ID NO: 1
```

FIG._1A

HEAVY CHAIN

```
1    EVQLVESGGGLVQPGGSLRLSCAASGFNIKDTYIHWVRQAPGKGL
46   EWVARIYPTNGYTRYADSVKGRFTISADTSKNTAYLQMNSLRAED
91   TAVYYCSRWGGDGFYAMDYWGQGTLVTVSSASTKGPSVFPLAPSS
136  KSTSGGTAALGCLVKDYFPEPVTVSWNSGALTSGVHTFPAVLQSS
181  GLYSLSSVVTVPSSSLGTQTYICNVNHKPSNTKVDKKVEPKSCDK
226  THTCPPCPAPELLGGPSVFLFPPKPKDTLMISRTPEVTCVVVDVS
271  HEDPEVKFNWYVDGVEVHNAKTKPREEQYNSTYRVVSVLTVLHQD
                                 =
316  WLNGKEYKCKVSNKALPAPIEKTISKAKGQPREPQVYTLPPSREE
361  MTKNQVSLTCLVKGFYPSDIAVEWESNGQPENNYKTTPPVLDSDG
                                            =
406  SFFLYSKLTVDKSRWQQGNVFSCSVMHEALHNHYTQKSLSLSPG  449
```

SEQ ID NO: 2

FIG._1B

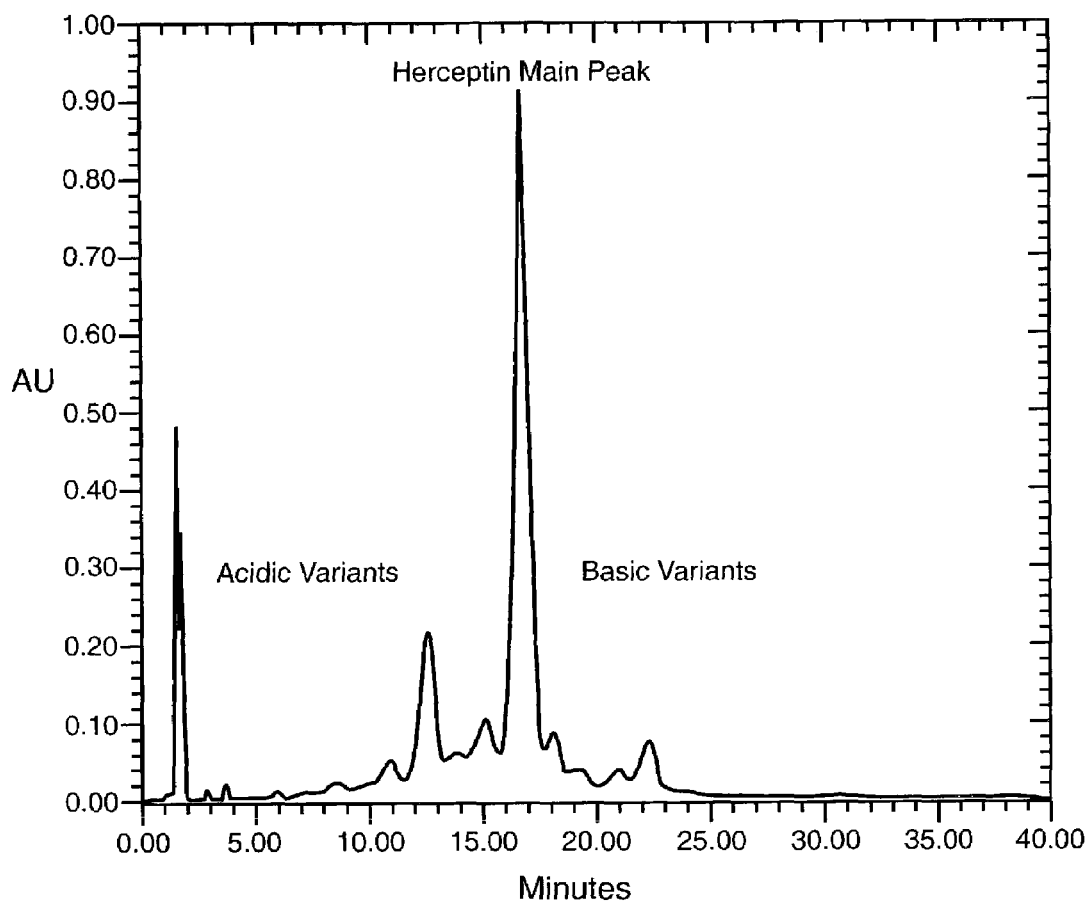
FIG._2

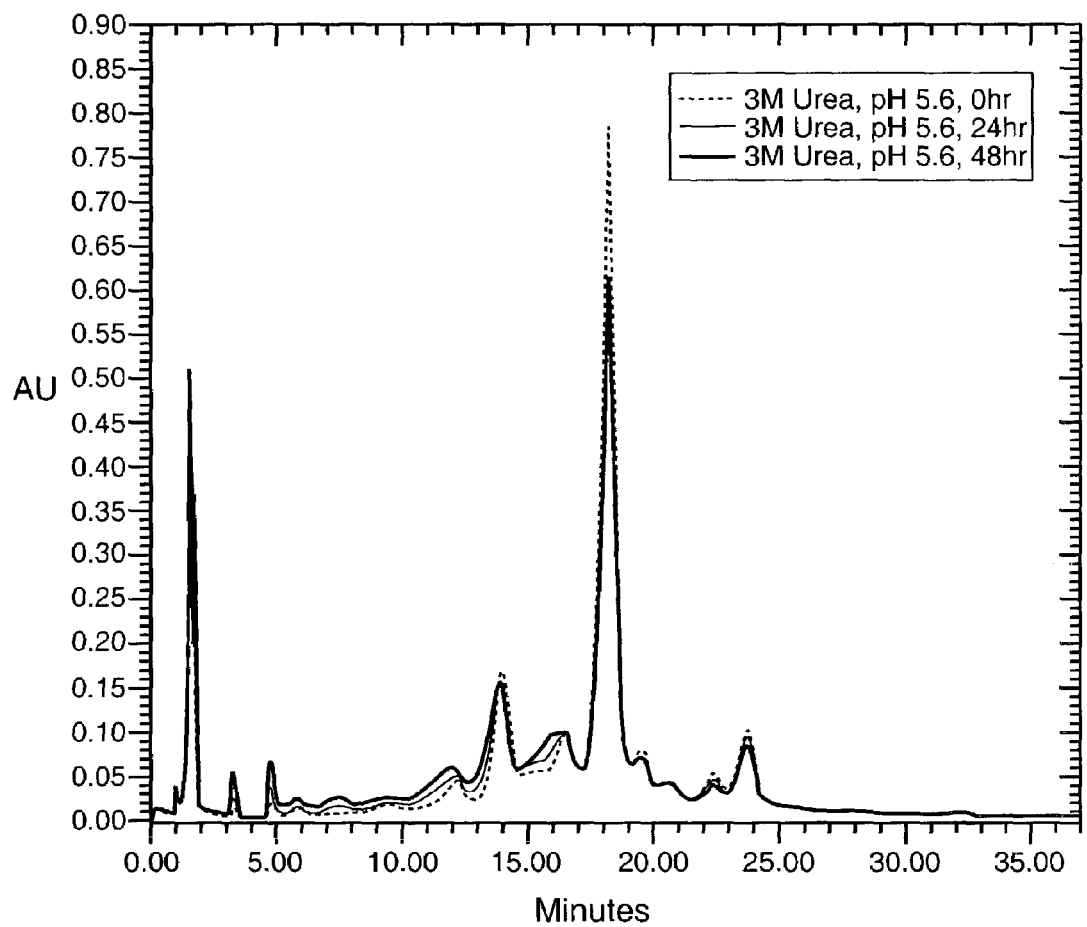
FIG._3

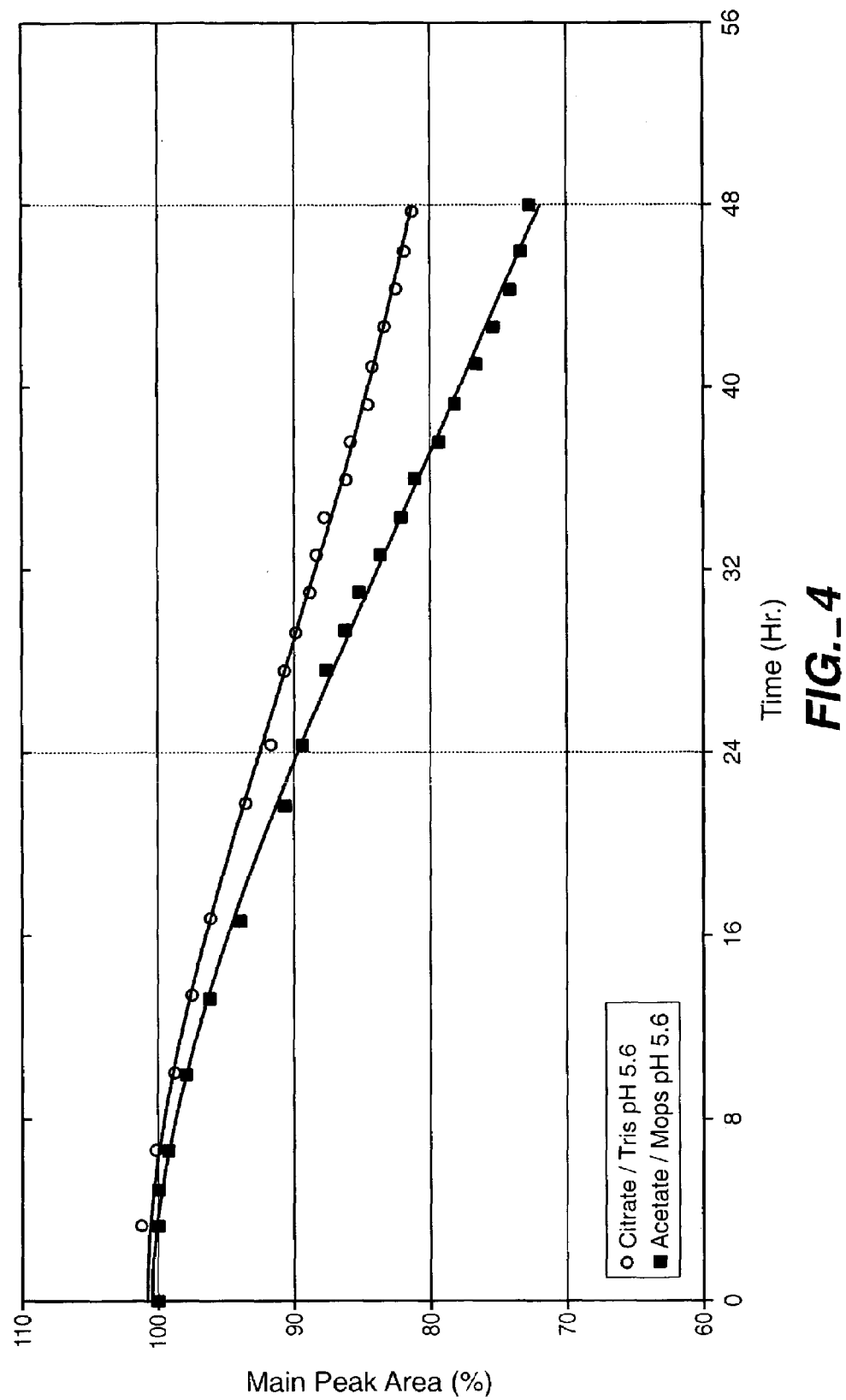
FIG._4

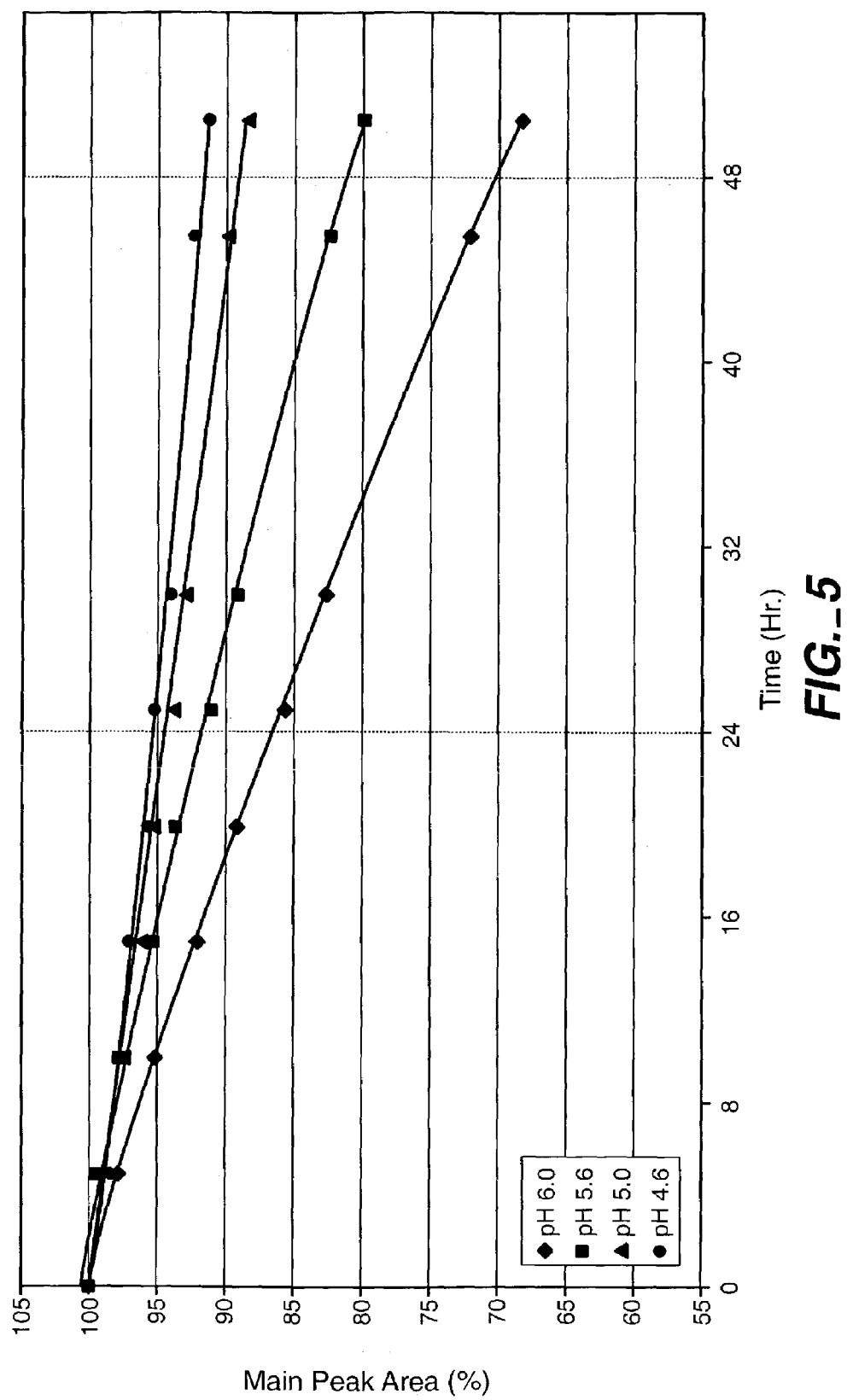
FIG._5

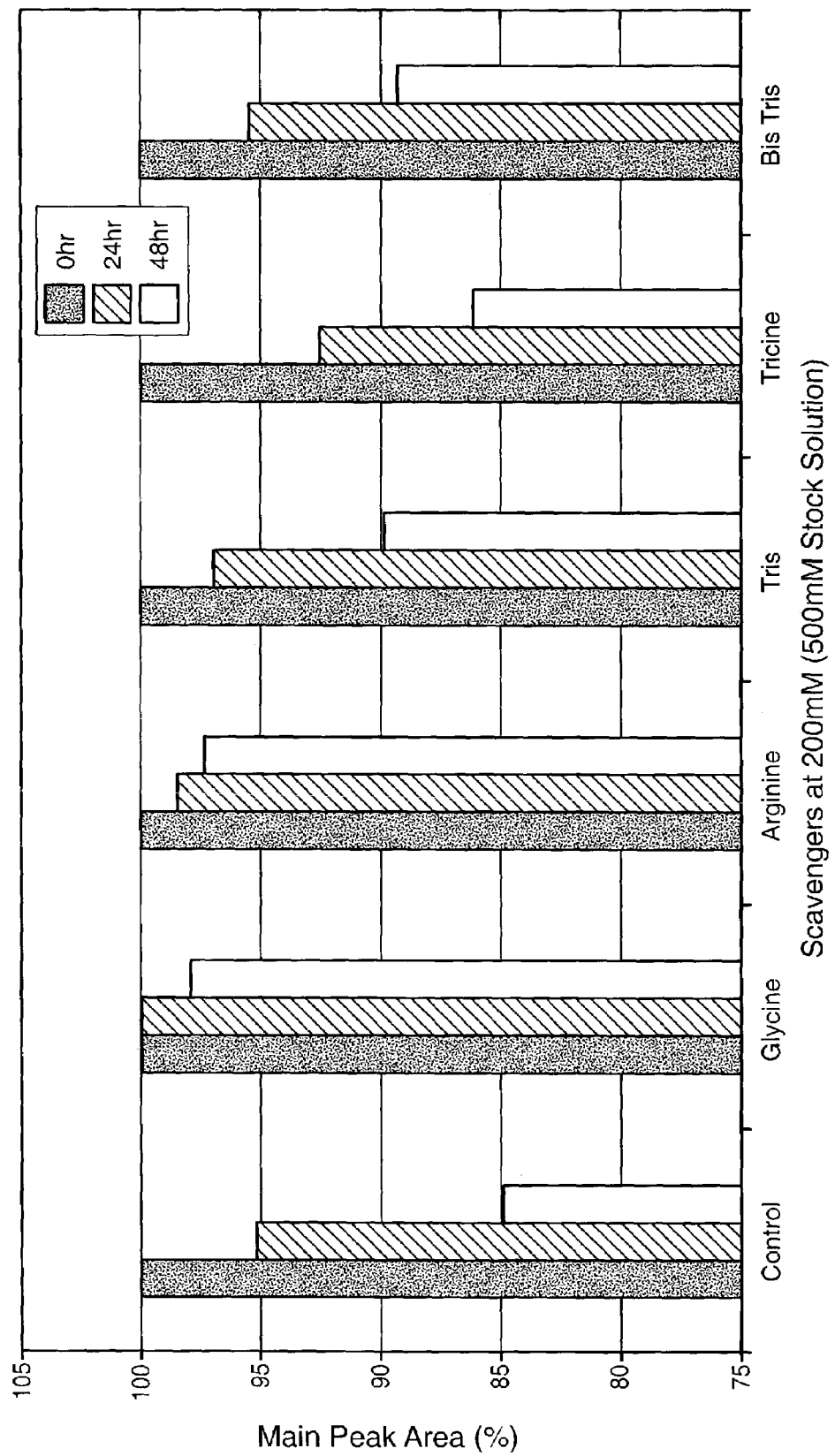
FIG._6

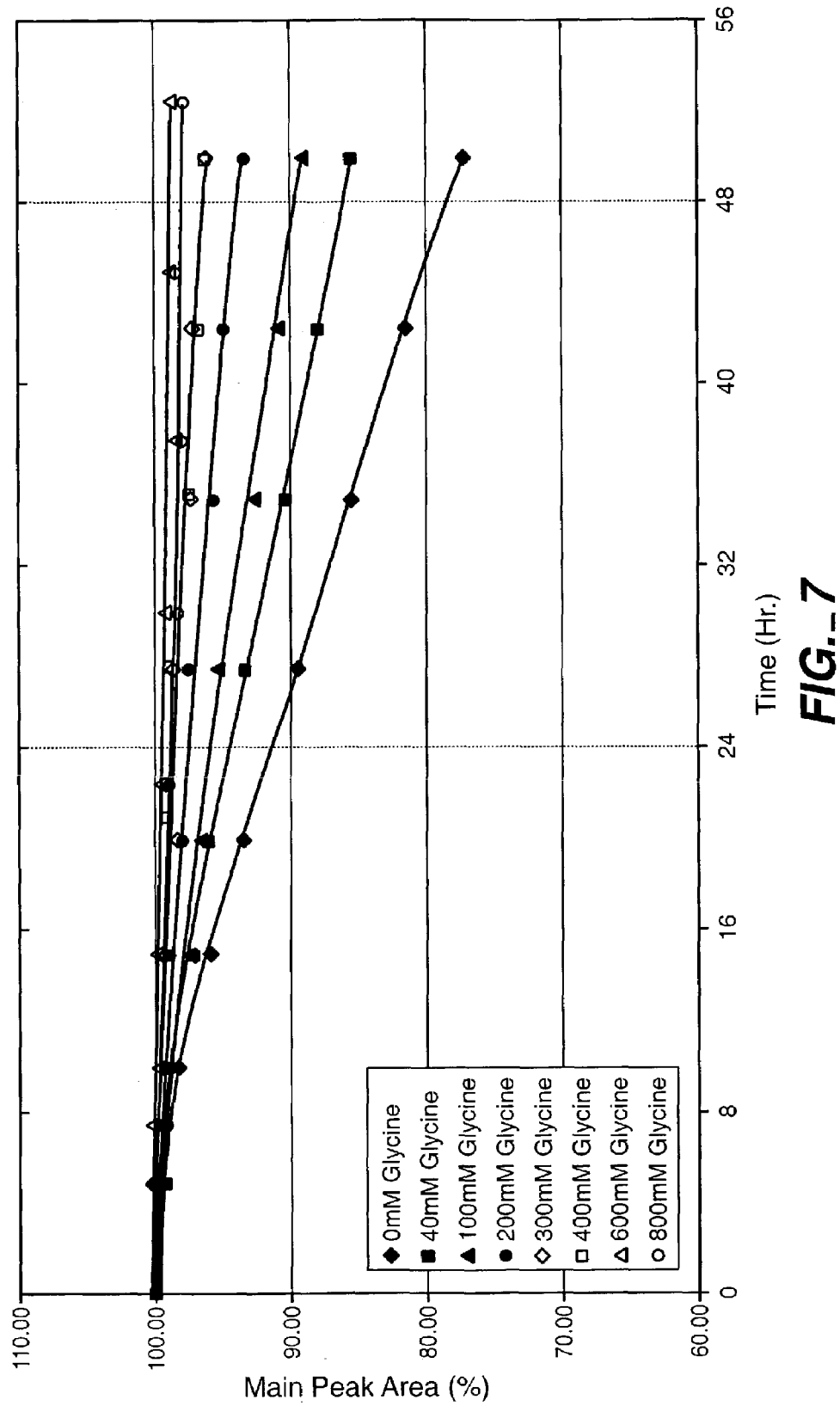
FIG._7

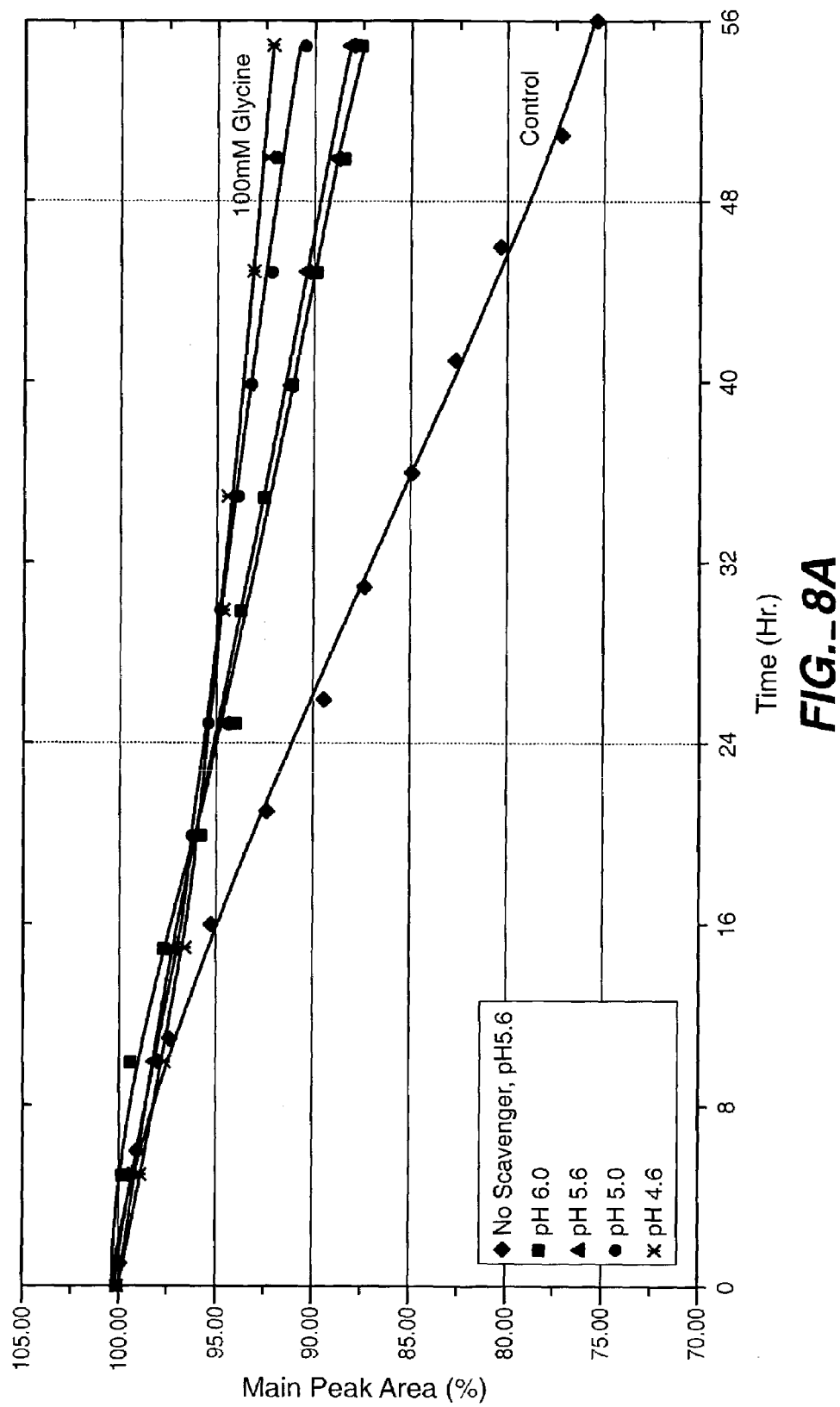
FIG._8A

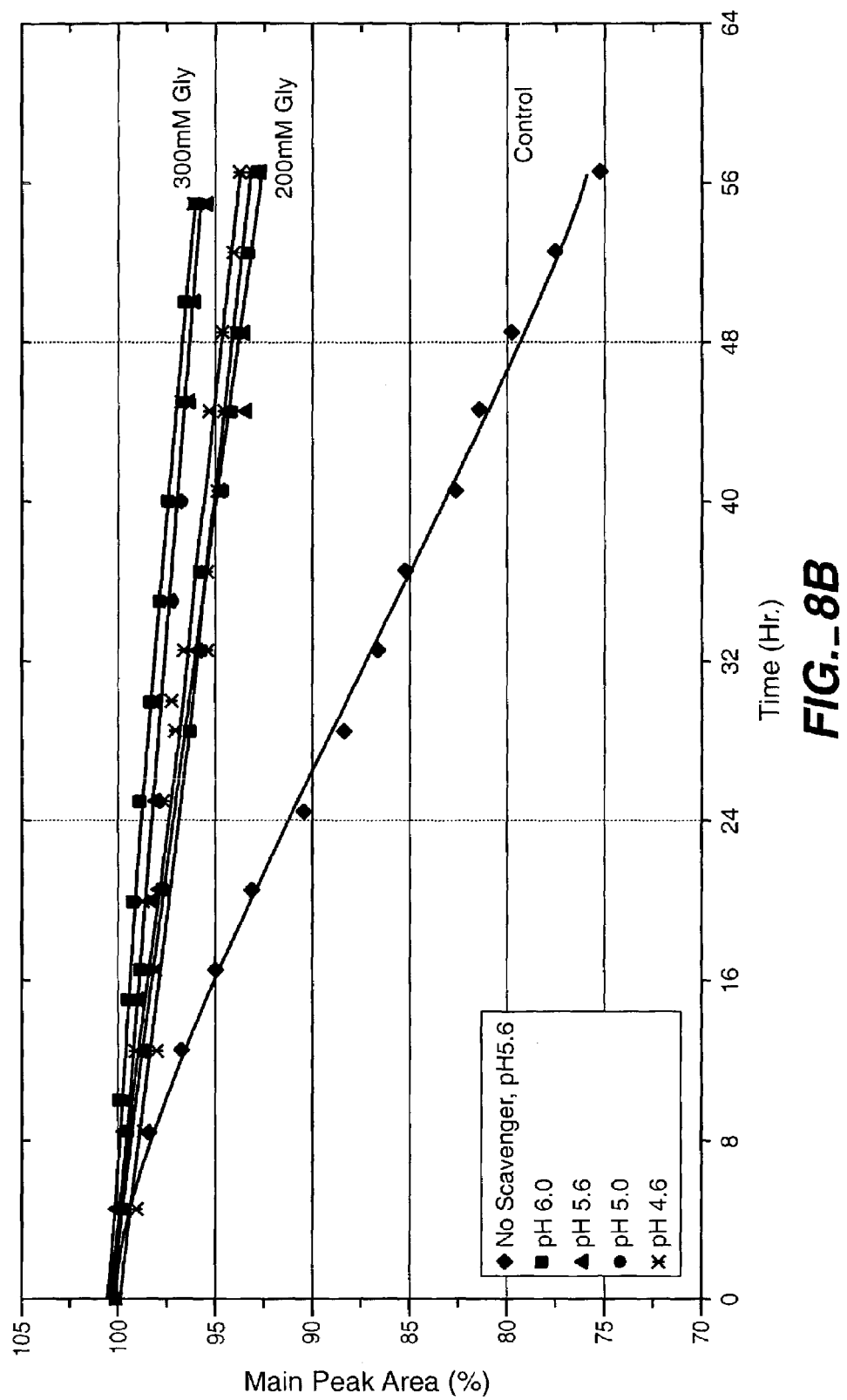
FIG._8B

STABILIZING POLYPEPTIDES WHICH HAVE BEEN EXPOSED TO UREA

RELATED APPLICATION

This application is a non-provisional application filed under 37 CFR 1.53(b)(1), claiming priority under 35 USC 119(e) to provisional application No. 60/341,891 filed Dec. 19, 2001, the contents of which are incorporated herein by reference.

BACKGROUND OF THE INVENTION

1. Field of the Invention

This invention relates generally to stabilizing polypeptides. In particular, the invention pertains to preventing or inhibiting degradation of a polypeptide, such as an antibody, where such degradation results from exposure of the polypeptide to urea.

2. Description of Related Art

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through".

U.S. Pat. No. 6,127,526 (Blank, G.) describes purifying proteins, such as anti-HER2 antibodies, by Protein A chromatography. WO99/57134 (Basey et al.) describes ion exchange chromatography for purifying polypeptides. The method is particularly useful for removing contaminating acidic antibody variants from the desired antibody product. U.S. Pat. No. 4,605,513 (Di Marchi, R.) refers to a process for inhibiting carbamylation of peptides using 1,2-ethylene diamine or 1,2-ethylene diamine-like materials.

SUMMARY OF THE INVENTION

The present invention provides a method for stabilizing a polypeptide (e.g. an antibody) from degradation upon exposure to urea comprising performing said exposure in the presence of an amine containing solution or a cyanate scavenger.

The invention also provides a method of preparing a polypeptide comprising treating a composition comprising the polypeptide and one or more viral contaminants with urea to inactivate the viral contaminant(s), wherein said treatment is performed in the presence of a cyanate scavenger.

The invention additionally provides a method of preparing a polypeptide comprising: (a) purifying the polypeptide by a first purification step; and (b) treating the polypeptide of step (a) with urea to inactivate viral contamination thereof, wherein said treatment is performed in the presence of a cyanate scavenger.

In addition, the invention provides a composition comprising an antibody (e.g. an anti-HER2 antibody), urea and a cyanate scavenger (e.g. glycine).

BRIEF DESCRIPTION OF THE DRAWINGS

FIGS. 1A-B shows the light chain amino acid sequence (SEQ ID NO:1) and heavy chain amino acid sequence (SEQ ID NO:2) of Trastuzumab (HERCEPTIN®).

FIG. 2 depicts a typical Trastuzumab (HERCEPTIN®) ion exchange profile.

FIG. 3 represents degradation of Trastuzumab (HERCEPTIN®) in the presence of 3M deionized urea at room temperature.

FIG. 4 illustrates Trastuzumab (HERCEPTIN®) main peak stability in citrate/Tris or acetate/Mops elution buffers at pH 5.6.

FIG. 5 shows the effect of pH on Trastuzumab (HERCEPTIN®) stability.

FIG. 6 reveals screening of amine containing solutions for their ability to improve Trastuzumab (HERCEPTIN®) stability in 3M urea, pH 5.6.

FIG. 7 demonstrates the effect of glycine concentration on Trastuzumab (HERCEPTIN®) stability.

FIGS. 8A and 8B reveal the combined effect of pH and glycine on Trastuzumab (HERCEPTIN®) stability.

DETAILED DESCRIPTION OF THE PREFERRED EMBODIMENTS

Definitions

As used herein, "polypeptide" refers generally to peptides and proteins having more than about ten amino acids. Preferably, the polypeptide is a mammalian protein, examples of which include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; integrins such as CD11a, CD11b, CD11c, CD18; an ICAM, VLA-4 and VCAM; a tumor associated antigen such as an ErbB receptor (e.g. EGFR, HER2, HER3 or HER4 receptor); an antibody; and fragments and/or variants of any of the above-listed polypeptides.

A "recombinant polypeptide" is one which has been produced in a host cell which has been transformed or transfected with nucleic acid encoding the polypeptide, or produces the polypeptide as a result of homologous recombination. "Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well as a cell within a genetically modified host animal or plant. Methods for recombinant production of polypeptides are described in U.S. Pat. No. 5,534,615, expressly incorporated herein by reference, for example.

A "contaminant" is a material that is different from the desired polypeptide product. The contaminant may be a viral contaminant, a variant of the desired polypeptide (e.g. an acidic variant or an amino-aspartate variant of the desired polypeptide) or another polypeptide, nucleic acid, endotoxin etc.

A "viral contaminant" refers to one or more viral agent(s) such as retroviruses, adventitious minute virus of mice (MVM), SV40, parvovirus, and cercovirus that may be present in a composition comprising the desired polypeptide and are preferably inactivated and/or removed from the composition.

By "viral inactivation" is meant killing or destroying a virus, such that it is no longer capable of infecting a cell.

By "stabilizing" herein is meant preventing or reducing to some extent degradation of a polypeptide of interest.

Herein, "degradation" refers to chemical or physical alteration of a polypeptide of interest, and includes aggregation, deamidation, isomerization, unfolding, carbamylation etc of the polypeptide.

A "deamidated" variant of a polypeptide molecule is a polypeptide wherein one or more asparagine residue(s) of the original polypeptide have been converted to aspartate, i.e. the neutral amide side chain has been converted to a residue with an overall acidic character. Deamidated Trastuzumab from the examples below has Asn30 in CDR1 of either or both of the $V_L$ regions thereof converted to aspartate.

"Urea" refers to a compound or composition comprising $NH_2CONH_2$ that can be used to inactivate viruses. Preferably the urea is deionized. Urea may decompose to form ammonium cyanate; $NH_4^+ + NCO^-$.

The term "exposure" herein refers to the combining of two or more compounds, such that there is physical or chemical interaction(s) between the two compounds. In the case of a polypeptide and urea, the exposure may result in degradation of the polypeptide.

The exposure of the polypeptide and urea may occur "in the presence of" an amine containing solution or cyanate scavenger, i.e. the amine containing solution or cyanate scavenger may be included with the urea, included with the polypeptide and/or added to a composition comprising the urea and polypeptide. Preferably, the amine containing solution or cyanate scavenger is added to the urea to yield a composition comprising the urea and amine containing solution or cyanate scavenger.

A "buffer" is a solution that resists changes in pH by the action of its acid-base conjugate components. Various buffers that can be employed depending, for example, on the desired pH of the buffer are described in *Buffers. A Guide for the Preparation and Use of Buffers in Biological Systems*, Gueffroy, D., Ed. Calbiochem Corporation (1975). In one embodiment, the buffer has a pH in the range from about 4 to about 6.5, preferably about pH 5.6.

An "amine containing solution" refers to a solution in which one or more of its constituents contains an amine group in its chemical structure, where an "amine group" is defined as NH2 or one of its derivatives. Preferred amine containing solutions comprise an amino acid such as glycine or arginine, or may be selected from a buffer such as Tris HCl, Bis Tris, or Tricine. The preferred amine containing solution comprises glycine. The amine containing solution may function as a cyanate scavenger.

By "cyanate scavenger" is meant a compound or composition which is able to chemically combine with cyanate. The preferred cyanate scavenger is glycine.

The amine containing solution or cyanate scavenger is used in an "amount effective to stabilize the polypeptide," i.e. such that degradation of the polypeptide due to urea exposure is significantly reduced compared to control treatment. Useful final concentrations of the amine containing solution or cyanate scavenger may be in the range from about 10 mM to about 1 M, and preferably from about 200 mM to about 400 mM. By "final concentration" here is meant the concentration of the amine containing solution or cyanate scavenger in a composition comprising the polypeptide, amine containing solution or cyanate scavenger, and urea.

The term "antibody" is used in the broadest sense and specifically covers monoclonal antibodies (including full length monoclonal antibodies), polyclonal antibodies. multispecific antibodies (e.g., bispecific antibodies), and antibody fragments so long as they exhibit the desired biological activity.

The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those polypeptides discussed above. Preferred molecular targets for antibodies encompassed by the present invention include CD polypeptides such as CD3, CD4, CD8, CD19, CD20, CD22, CD34 and CD40; ErbB receptors such as the EGF receptor, HER2, HER3 or HER4 receptor; cell adhesion molecules such as LFA-1, Mac1, p150,95, VLA-4, ICAM-1, VCAM and av/b3 integrin including either a or b subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). In a further embodiment, "monoclonal antibodies" can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Polypeptides of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). In another embodiment, the F(ab')$_2$ is formed using the leucine zipper GCN4 to promote assembly of the F(ab')$_2$ molecule. According to another approach, F(ab')$_2$ fragments can be isolated directly from recombinant host cell culture. Other techniques for the production of antibody fragments will be apparent to the skilled practitioner.

In other embodiments, the antibody of choice is a single chain Fv fragment (scFv). See WO 93/16185. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" when used throughout this application refers to the antibodies described in Zapata et al. *Polypeptide Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

"Multispecific antibodies" have binding specificities for at least two different epitopes, where the epitopes are usually from different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1I, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti -saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti- CD37. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan) Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

By "purifying" a polypeptide from a composition comprising the polypeptide and one or more contaminants is meant increasing the degree of purity of the polypeptide in the composition by removing (completely or partially) at least one contaminant from the composition.

Unless indicated otherwise, the term "HER2" when used herein refers to human HER2 protein and "HER2" refers to human HER2 gene. The human HER2 gene and HER2 protein are described in Semba et al., *PNAS* (USA) 82:6497-6501 (1985) and Yamamoto et al. *Nature* 319:230-234 (1986) (Genebank accession number X03363), for example.

"Trastuzumab" or "HERCEPTIN®" is a humanized anti-HER2 antibody comprising the light chain amino acid sequence of SEQ ID NO:1 and the heavy chain amino acid sequence of SEQ ID NO:2 or amino acid sequence variants thereof which retain the ability to bind HER2 and inhibit growth of tumor cells which overexpress HER2 (see U.S. Pat. No. 5,677,171; expressly incorporated herein by reference).

MODES FOR CARRYING OUT THE INVENTION

The invention relates to the preparation, or treatment of, a polypeptide. The polypeptide is generally recombinantly produced, but may be produced by peptide synthesis (or other synthetic means) or purified from a native source of the polypeptide.

Preferably, the polypeptide is an antibody. Preferred antibodies within the scope of the present invention include anti-HER2 antibodies including Trastuzumab (HERCEPTIN®) (Carter et al., *Proc. Natl. Acad. Sci. USA,* 89:4285-4289 (1992), U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108, B1 or Tositumomab (BEXXAR®); anti-IL-8 (St John et al., *Chest,* 103:932 (1993), and International Publication No. WO 95/23865); anti-VEGF antibodies including humanized and/or affinity matured anti-VEGF antibodies such as the humanized anti-VEGF antibody huA4.6.1 AVASTIN™ (Kim et al., *Growth Factors,* 7:53-64 (1992), International Publication No. WO 96/30046, and WO 98/45331, published Oct. 15, 1998); anti-prostate stem cell antigen (PSCA) antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3-7 (1991), and Hourmant et al., *Transplantation* 58:377-380 (1994)); anti-IgE (Presta et al., *J. Immunol.* 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-$\alpha$ antibodies including cA2 (REMICADE®), CDP571 and MAK-195 (See, U.S. Pat. No. 5,672,347 issued Sep. 30, 1997, Lorenz et al. *J. Immunol.* 156(4): 1646-1653 (1996), and Dhainaut et al. *Crit. Care Med.* 23(9): 1461-1469 (1995)); anti-Tissue Factor (TF) (European Patent No. 0 420 937 B1 granted Nov. 9, 1994); anti-human $\alpha_4$-$\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. *Arthritis Rheum* 39(1):52-56 (1996)); anti-CD52 antibodies such as CAMPATH-1H (Riechmann et al. *Nature* 332:323-337 (1988); anti-Fc receptor antibodies such as the M22 antibody directed against Fc$\gamma$RI as in Graziano et al. *J. Immunol.* 155(10):4996-5002 (1995); anti-carcinoembryonic antigen (CEA) antibodies such as hMN-14 (Sharkey et al. *Cancer Res.* 55(23Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J. Immunol.* 26(1):1-9 (1996)); anti-CD38 antibodies, e.g. AT 13/5 (Ellis et al. *J. Immunol.* 155(2):925-937 (1995)); anti-CD33 antibodies such as Hu M195 (Jurcic et al. *Cancer Res* 55(23 Suppl): 5908s-5910s (1995) and CMA-676 or CDP771; anti-CD22 antibodies such as LL2 or LymphoCide (Juweid et al. *Cancer Res* 55(23 Suppl):5899s-5907s (1995); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-$\alpha$v$\beta$3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2, VEGF, IgE, CD20, CD11a, CD40, tissue factor (TF), prostate stem cell antigen (PSCA), IL8, HER3, HER4, epidermal growth factor receptor (EGFR), CD18, $\alpha_4\beta_7$, and $\alpha_5\beta_3$.

For recombinant production of the polypeptide, the nucleic acid encoding it is isolated and inserted into a replicable vector for further cloning (amplification of the DNA) or for expression. DNA encoding the polypeptide is readily isolated and sequenced using conventional procedures (e.g., where the polypeptide is an antibody by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g. as described in U.S. Pat. No. 5,534,615, specifically incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli , Enterobacter, Erwinia, Klebsiella, Proteus, Salmonella*, e.g., *Salmonella typhimurium , Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces*

*pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus ; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger.*

Suitable host cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx Mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

The host cells used to produce the polypeptide of this invention may be cultured in a variety of media. Commercially available media such as Ham's F10 (Sigma), Minimal Essential Medium ((MEM), (Sigma), RPMI-1640 (Sigma), and Dilbecen's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the polypeptide can be produced intracellularly, in the periplasmic space, or directly secreted into the medium. If the polypeptide is produced intracellularly, as a first step, the particulate debris, either host cells or lysed cells (e.g. resulting from homogenization), is removed, for example, by centrifugation or ultrafiltration. Where the polypeptide is secreted into the medium, supernatants from such expression systems are generally first concentrated using a commercially available protein concentration filter, for example, an Amicon or Millipore Pellicon ultrafiltration unit.

The polypeptide may be subjected to one or more purification steps prior to viral inactivation. Examples of purification procedures which may be performed prior to, during, or following viral inactivation include fractionation on a hydrophobic interaction chromatography (e.g. on phenyl sepharose), ethanol precipitation, isoelectric focusing, Reverse Phase HPLC, chromatography on silica, chromatography on HEPARIN SEPHAROSE™, anion exchange chromatography, cation exchange chromatography, chromatofocusing, SDS-PAGE, ammonium sulfate precipitation, hydroxylapatite chromatography, gel electrophoresis, dialysis, and affinity chromatography (e.g. using protein A, protein G, an antibody, a specific substrate, ligand or antigen as the capture reagent.

The invention herein pertains, at least in part, to inactivating viral contamination of the polypeptide, especially where the polypeptide is an anti-HER2 antibody such as Trastuzumab. The viral contamination may occur due to the use of recombinant host cells or animals, or cell culturing materials containing viruses, or to the presence of viruses in a natural source of the polypeptide from which it is to be recovered.

In the preferred embodiment herein, viral inactivation is preceded by at least one purification step. In the case of an antibody, such as the anti-HER2 antibody herein, the purification step is Protein A chromatography.

According to the invention herein, the composition comprising the polypeptide and the viral contaminant(s) is exposed to urea to inactivate viruses in the composition. For the anti-HER2 composition, urea added to a 3M final concentration at pH 5.6 is anticipated to give at least 4 logs of viral inactivation. Hence, according to at least the preferred embodiment of the invention, from about 2 M to about 4 M (e.g. about 3M) urea at a pH from about 4 to about 6.5 (and preferably about pH 5.6) is added to the composition of the polypeptide with viral contamination. Further treatments to inactivate or remove viral contaminants may be included, such as lowering pH (e.g. to about 3.9), viral filtration, or other purification procedure(s), such as column chromatography, that remove viruses. Such further viral inactivation/removal treatments may be carried out prior to, simultaneously with, or following the urea treatment.

The examples below demonstrate that addition of urea to a polypeptide, such as the anti-HER2 antibody Trastuzumab, can degrade the polypeptide by increasing the number and/or quantity of acidic variant(s) compared to the desired non-degraded polypeptide, increasing aggregation of the polypeptide, and/or by causing unfolding of the polypeptide, for instance. Such degradation can be measured using standard methodology, such as ion exchange chromatography to resolve the desired polypeptide and charge variants thereof; circular dichroism for determining unfolding of the polypeptide; size exclusion HPLC analysis for assessing aggregation of the polypeptide; papain digestion and mass spectrometry for measuring carbamylation.

Where degradation of the polypeptide due to exposure to urea is observed, the present invention provides a method for stabilizing a polypeptide from such degradation through the use of a cyanate scavenger or amine containing solution to prevent (to some extent) or reduce (to some degree) degradation of the polypeptide.

The cyanate scavenger or amine containing solution can for instance be added to the urea, added to the polypeptide, and/or added to the composition comprising the urea and polypeptide. Preferably, the cyanate scavenger or amine containing solution is added to the urea in an amount effective to stabilize the polypeptide. Such concentrations may be determined by adding varying concentrations of the scavenger or amine containing solution to the urea and measuring polypeptide degradation as in Example 4 for instance. It is contemplated that a final concentration from about 200 mM to about 300 mM of the cyanate scavenger or amine containing solution will be added to the urea. Based on its stabilizing properties (for inhibiting/preventing polypeptide deamidation or unfolding compared to control), high solubility in urea, low conductivity at high concentrations (for binding to the cation exchange column) and low cost compared to the other scavengers tested, glycine is considered to be a particularly desirable agent for stabilizing the polypeptide.

Glycine was found to be preferably added to the urea at a final concentration of about 200 nM to about 400 mM. Preferably the pH of the composition comprising the polypeptide, urea and glycine is about 4-6.5, and most preferably about 5.6.

After the viral inactivation step, the composition comprising the polypeptide, urea and scavenger/amine containing solution is subjected to one or more downstream purification steps which reduce or remove the urea, scavenger/amine containing solution, inactivated viruses (and other contaminants), from the composition. Various purification procedures have been described above, with cation exchange chromatography (e.g. as in WO99/57134) and anion exchange chromatography being preferred downstream purification methods for removing further contaminants.

Optionally, the polypeptide is conjugated to one or more heterologous molecules as desired. The heterologous molecule may, for example, be one which increases the serum half-life of the polypeptide (e.g. polyethylene glycol, PEG), or it may be a label (e.g. an enzyme, fluorescent label and/or radionuclide) or a cytotoxic molecule (e.g. a toxin, chemotherapeutic drug, or radioactive isotope etc).

A therapeutic formulation comprising the polypeptide, optionally conjugated with a heterologous molecule, may be prepared by mixing the polypeptide having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. "Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The Trastuzumab antibody of particular interest herein may be prepared as a lyophilized formulation, e.g. as described in WO 97/04801; expressly incorporated herein by reference.

The formulation herein may also contain more than one active compound as necessary for the particular indication being treated, preferably those with complementary activities that do not adversely affect each other. Such molecules are suitably present in combination in amounts that are effective for the purpose intended. For example, for an anti-HER2 antibody a chemotherapeutic agent, such as a taxoid or tamoxifen, may be added to the formulation.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulation to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide variant, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The polypeptide purified as disclosed herein or the composition comprising the polypeptide and a pharmaceutically acceptable carrier is then used for various diagnostic, therapeutic or other uses known for such polypeptides and compositions. For example, the polypeptide may be used to treat a disorder in a mammal by administering a therapeutically effective amount of the polypeptide to the mammal.

The following examples are offered by way of illustration and not by way of limitation. The disclosures of all citations in the specification are expressly incorporated herein by reference.

EXAMPLE 1

Resolution of Trastuzumab and its Variants

Trastuzumab (HERCEPTIN®) is a recombinant, humanized antibody directed against the HER2 antigen that is approved for the treatment of metastatic breast cancer.

The stability of Trastuzumab can be determined using a cation exchange (Dionex) assay for resolution of Trastuzumab into its variants through elution in a 15-100 mM NaCl gradient. A typical Trastuzumab ion exchange profile is shown in FIG. 2.

The logs of viral inactivation for Trastuzumab purified using Protein A chromatography, hydrophobic interaction chromatograph (HIC), and anion exchange chromatography are shown in the following table.

TABLE 1

| Step | Logs of Viral Inactivation | | |
|---|---|---|---|
| | Retrovirus | MVM (Adventitous) | SV40 (Adventitous) |
| Protein A | 3.5 | 2.5 | 2.5 |
| Low pH | 5.6 | — | |
| SP Sepharose | 2.4 | — | |
| Q Sepharose | 3.7 | 5.5 | 2.5 |
| HIC | 1.4 | — | |

EXAMPLE 2

Stability of Trastuzumab in Urea 3M urea at pH 5.6 was thought to give at least 4 logs of viral inactivation. To achieve this, a 7.5M stock of urea was prepared and deionized. This was added to Trastuzumab Protein A elution pool to yield a final concentration of 3M. This pool was then adjusted to pH 5.6. At regular intervals, samples were analyzed by the Dionex assay. Urea was found to degrade Trastuzumab at room temperature as determined by the reduction in the "main peak" and increase in acidic variants (FIG. 3). With time, the main peak was converted into acidic variants. Analyzing the drop in main peak area was deemed a suitable method of measuring stability.

At pH 5.6, Trastuzumab was more stable in a citrate/Tris buffer than an acetate/Mops buffer (FIG. 4).

As pH was decreased, an improvement in stability was observed (FIG. 5).

EXAMPLE 3

Improving Trastuzumab Stability

Various scavengers of free cyanate ions were screened for their ability to stabilize Trastuzumab in the presence of urea. The scavenger was desirably an amine containing solution which was readily soluble in urea. The scavengers tested were: Tris HCl, Bis Tris, Tricine, Bis Tris Propyl, Arginine, Glycine (see FIG. 6). The cost, pool conductivity, and released material status of these scavengers is reflected in the following table.

TABLE 2

| | Potential Scavengers | | |
|---|---|---|---|
| Molecule | Cost of 500 mM/L Stock ($) | Pool Conductivity (mS/cm) | Released Material |
| Glycine | 0.33 | 4.5 | Yes |
| Arginine | 1.92 | 15.5 | Yes |
| Tris HCl | 1.98 | 16.4 | Yes |
| Tricine | 7.17 | 4.2 | Yes |
| Bis Tris | — | 14.5 | No |
| Bis Tris Propyl | — | 23.0 | No |

Glycine was selected as the preferred due to its effectiveness at maintaining the main peak area, its high solubility, low conductivity at high concentrations and low cost relative to other scavengers. Glycine is also a released material (i.e. it is approved by Quality Control for GMP).

EXAMPLE 4

Use of Glycine to Stabilize Trastuzumab

The effect of glycine concentration on Trastuzumab stability in the presence of urea was assessed. Initial and final glycine concentrations are reflected in the following table.

TABLE 3

| Glycine Concentration Range | |
|---|---|
| Initial Conc. (mM) | Final Conc. (mM) |
| 100 | 40 |
| 250 | 100 |
| 500 | 200 |
| 750 | 300 |
| 1000 | 400 |
| 1500 | 600 |
| 2000 | 800 |

At a final concentration greater than 300 mM, there was no significant increase in stability (FIG. 7).

The combined effect of pH and glycine on Trastuzumab stability was assessed (see FIGS. 8A and 8B). At a glycine concentration of 100 mM, the effect of pH on stability could still be seen. However, the presence of glycine at higher concentrations negated the effect of pH.

EXAMPLE 5

Carbamylation Analysis

Carbamylation of Trastuzumab incubated in 3M urea was assessed. Samples were first papain digested and then analyzed by mass spectrometry to assess carbamylation. Four conditions were assessed (1) no pH adjustment, 3M urea; (2) pH 5.6, 3M urea; (3) no pH adjustment, 3M urea, 300 mM glycine; and (4) pH 5.6, 3M urea, 300 mM glycine. No significant differences in carbamylation were observed for the different conditions examined.

The invention claimed is:

1. A method for stabilizing an antibody from degradation upon exposure to urea comprising determining that said antibody shows degradation upon exposure to urea, exposing said antibody to urea in the presence of an amine containing solution comprising an amino acid, and confirming that degradation of said antibody has been prevented or reduced.

2. The method of claim 1 wherein the amino acid is glycine.

3. The method of claim 2 wherein the concentration of the glycine is from about 100 mM to about 400 mM.

4. The method of claim 1 wherein the antibody binds HER2, vascular endothelial growth factor (VEGF), IgE, CD20, CD40, CD11a, tissue factor (TF), prostate stem cell antigen (PSCA), interleukin-8 (IL-8), epidermal growth factor receptor (EGFR), HER3, HER4, $\alpha 4\beta 7$ or $\alpha 5\beta 3$.

5. The method of claim 1 wherein the antibody is Trastuzumab (HERCEPTIN®).

6. The method of claim 1 wherein the antibody is exposed to urea to inactivate viral contaminant(s) in a composition comprising the antibody and the viral contaminant(s).

7. The method of claim 1 wherein the amine containing solution comprising an amino acid is added to urea prior to the exposure to the antibody.

8. The method of claim 1 wherein the concentration of the amine containing solution comprising an amino acid is from about 10 mM to about 1M.

9. The method of claim 1 wherein the antibody has been subjected to a purification step prior to the exposure to the urea.

10. The method of claim 9 wherein the purification step is Protein A chromatography.

11. The method of claim 1 which reduces deamidation, aggregation and/or unfolding of the antibody.

12. A method of preparing a monoclonal antibody comprising treating a composition comprising the monoclonal antibody and one or more viral contaminants with urea to inactivate the viral contaminant(s), wherein said treatment is performed in the presence of an amine-containing solution comprising an amino acid as a cyanate scavenger.

13. A method of inactivating or reducing viral contamination in a composition comprising an anti-HER2 antibody and one or more viral contaminant(s) comprising treating the composition with urea, in the presence of an amine-containing solution comprising an amino acid as a cyanate scavenger.

14. The method of claim 13 wherein urea is added to the anti-HER2 antibody composition at a concentration from about 2M to about 4M.

15. The meted of claim 13 wherein the pH of the composition is from about 4 to about 6.5.

16. An isolated composition comprising an anti-HER2 antibody, and urea and an amino acid added to said antibody, wherein the concentration of said antibody in the composition is from about 1 mg/mL to about 10 mg/mL.

17. An isolated composition comprising a anti-HER2 antibody, and urea ad a amino acid added to said antibody, wherein the concentration of said urea in the composition is from about 2M to about 4M.

18. An isolated composition comprising an anti-HER2 antibody, and urea and an amino acid added to said antibody, wherein the concentration of the amino acid is from about 200 mM to about 400 mM.

19. A method of preparing a polypeptide comprising:
(a) purifying the polypeptide by a first purification step; and
(b) treating the polypeptide of step (a) with urea to inactivate viral contamination thereof,
wherein said treatment is performed in to presence of a amine-containing solution comprising an amino acid as a cyanate scavenger.

20. The method of claim 19 wherein the amino acid is glycine.

21. The method of claim 19 wherein the polypeptide is an antibody and the purification step is Protein A Chromatography.

22. The method of claim 19 further comprising subjecting the polypeptide of step (b) to one or more additional purification step(s) which reduce the levels of urea and cyanate scavenger associated with the polypeptide.

* * * * *

UNITED STATES PATENT AND TRADEMARK OFFICE
CERTIFICATE OF CORRECTION

| | | |
|---|---|---|
| PATENT NO. | : 7,452,539 B2 | Page 1 of 1 |
| APPLICATION NO. | : 10/316694 | |
| DATED | : November 18, 2008 | |
| INVENTOR(S) | : Emery et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 574 days Delete the phrase "by 574 days" and insert -- by 1162 days --

Signed and Sealed this

First Day of June, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 1

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Arg Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                  100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys
```

<210> SEQ ID NO 2
<211> LENGTH: 449
<212> TYPE: PRT
<213> ORGANISM: Artificial sequence
<220> FEATURE:
<223> OTHER INFORMATION: Sequence is synthesized.

<400> SEQUENCE: 2

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
                35                  40                  45

Glu Trp Val Ala Arg Ile Tyr Pro Thr Asn Gly Tyr Thr Arg Tyr
                50                  55                  60
```

-continued

```
Ala Asp Ser Val Lys Gly Arg Phe Thr Ile Ser Ala Asp Thr Ser
             65                  70                  75
Lys Asn Thr Ala Tyr Leu Gln Met Asn Ser Leu Arg Ala Glu Asp
             80                  85                  90
Thr Ala Val Tyr Tyr Cys Ser Arg Trp Gly Asp Gly Phe Tyr
             95                 100                 105
Ala Met Asp Tyr Trp Gly Gln Gly Thr Leu Val Thr Val Ser Ser
            110                 115                 120
Ala Ser Thr Lys Gly Pro Ser Val Phe Pro Leu Ala Pro Ser Ser
            125                 130                 135
Lys Ser Thr Ser Gly Gly Thr Ala Ala Leu Gly Cys Leu Val Lys
            140                 145                 150
Asp Tyr Phe Pro Glu Pro Val Thr Val Ser Trp Asn Ser Gly Ala
            155                 160                 165
Leu Thr Ser Gly Val His Thr Phe Pro Ala Val Leu Gln Ser Ser
            170                 175                 180
Gly Leu Tyr Ser Leu Ser Ser Val Val Thr Val Pro Ser Ser Ser
            185                 190                 195
Leu Gly Thr Gln Thr Tyr Ile Cys Asn Val Asn His Lys Pro Ser
            200                 205                 210
Asn Thr Lys Val Asp Lys Lys Val Glu Pro Lys Ser Cys Asp Lys
            215                 220                 225
Thr His Thr Cys Pro Pro Cys Pro Ala Pro Glu Leu Leu Gly Gly
            230                 235                 240
Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn
            290                 295                 300
Ser Thr Tyr Arg Val Val Ser Val Leu Thr Val Leu His Gln Asp
            305                 310                 315
Trp Leu Asn Gly Lys Glu Tyr Lys Cys Lys Val Ser Asn Lys Ala
            320                 325                 330
Leu Pro Ala Pro Ile Glu Lys Thr Ile Ser Lys Ala Lys Gly Gln
            335                 340                 345
Pro Arg Glu Pro Gln Val Tyr Thr Leu Pro Pro Ser Arg Glu Glu
            350                 355                 360
Met Thr Lys Asn Gln Val Ser Leu Thr Cys Leu Val Lys Gly Phe
            365                 370                 375
Tyr Pro Ser Asp Ile Ala Val Glu Trp Glu Ser Asn Gly Gln Pro
            380                 385                 390
Glu Asn Asn Tyr Lys Thr Thr Pro Pro Val Leu Asp Ser Asp Gly
            395                 400                 405
Ser Phe Phe Leu Tyr Ser Lys Leu Thr Val Asp Lys Ser Arg Trp
            410                 415                 420
Gln Gln Gly Asn Val Phe Ser Cys Ser Val Met His Glu Ala Leu
            425                 430                 435
His Asn His Tyr Thr Gln Lys Ser Leu Ser Leu Ser Pro Gly
            440                 445
```